US011001782B2

(12) United States Patent
Dennis et al.

(10) Patent No.: US 11,001,782 B2
(45) Date of Patent: May 11, 2021

(54) METHODS OF RECOVERING OIL FROM MICROORGANISMS

(71) Applicant: DSM NUTRITIONAL PRODUCTS AG, Kaiseraugst (CH)

(72) Inventors: Dorothy A. Dennis, Halifax (CA); Roberto E. Armenta, Dartmouth (CA)

(73) Assignee: DSM Nutritional Products AG, Kaiseraugst (CH)

( * ) Notice: Subject to any disclaimer, the term of this patent is extended or adjusted under 35 U.S.C. 154(b) by 183 days.

(21) Appl. No.: 15/104,472

(22) PCT Filed: Dec. 19, 2014

(86) PCT No.: PCT/IB2014/003113
§ 371 (c)(1),
(2) Date: Jun. 14, 2016

(87) PCT Pub. No.: WO2015/092544
PCT Pub. Date: Jun. 25, 2015

(65) Prior Publication Data
US 2016/0312147 A1    Oct. 27, 2016

Related U.S. Application Data

(60) Provisional application No. 61/918,880, filed on Dec. 20, 2013.

(51) Int. Cl.
*C11B 3/00* (2006.01)
*C12P 7/64* (2006.01)

(52) U.S. Cl.
CPC ............ *C11B 3/003* (2013.01); *C12P 7/6409* (2013.01)

(58) Field of Classification Search
CPC . C12P 7/6409; C11B 1/10; C11B 1/00; C11B 3/003
See application file for complete search history.

(56) References Cited

U.S. PATENT DOCUMENTS

| | | |
|---|---|---|
| 2,753,362 A | 7/1956 | Owades et al. |
| 3,089,821 A | 5/1963 | Folkers |
| 4,504,473 A | 3/1985 | Cantrell |
| 4,720,456 A | 1/1988 | Wagner et al. |
| 4,792,418 A | 12/1988 | Rubin et al. |
| 4,906,746 A | 3/1990 | Barnier et al. |
| 5,130,242 A | 7/1992 | Barclay et al. |
| 5,173,409 A | 12/1992 | English |
| 5,179,012 A | 1/1993 | Gudin et al. |
| 5,338,673 A | 8/1994 | Thepenier et al. |
| 5,340,594 A | 8/1994 | Barclay et al. |
| 5,340,742 A | 8/1994 | Barclay et al. |
| 5,397,591 A | 3/1995 | Kyle et al. |
| 5,492,938 A | 2/1996 | Kyle et al. |
| 5,539,133 A | 7/1996 | Kohn et al. |
| 5,897,994 A | 4/1999 | Sandoz et al. |
| 5,928,696 A | 7/1999 | Hegwein et al. |
| 6,166,231 A | 12/2000 | Hoeksema |
| 6,180,376 B1 | 1/2001 | Liddell |
| 6,255,505 B1 | 7/2001 | Bijl et al. |
| 6,344,349 B1 | 2/2002 | Moldavsky et al. |
| 6,447,782 B1 | 9/2002 | Viron et al. |
| 6,451,567 B1 | 9/2002 | Barclay |
| 6,509,178 B1 | 1/2003 | Tanaka et al. |
| 6,582,941 B1 | 6/2003 | Yokochi et al. |
| 6,607,900 B2 | 8/2003 | Bailey et al. |
| 6,750,048 B2 | 6/2004 | Ruecker et al. |
| 6,812,001 B2 | 11/2004 | Sibeijn et al. |
| 7,351,558 B2 | 4/2008 | Ruecker et al. |
| 7,431,952 B2 | 10/2008 | Bijl et al. |
| 7,662,598 B2 | 2/2010 | Ruecker et al. |
| 7,781,193 B2 | 8/2010 | Ruecker et al. |
| 2005/0170479 A1 | 8/2005 | Weaver et al. |
| 2008/0038800 A1 | 2/2008 | Ruecker et al. |
| 2008/0044876 A1 | 2/2008 | Ruecker et al. |
| 2009/0117194 A1 | 5/2009 | Burja et al. |
| 2011/0295028 A1 | 12/2011 | Cherinko et al. |
| 2012/0135479 A1 | 5/2012 | Dillon et al. |
| 2012/0244584 A1 | 9/2012 | Zhang et al. |
| 2014/0212936 A1 | 7/2014 | Ruecker et al. |

(Continued)

FOREIGN PATENT DOCUMENTS

| | | |
|---|---|---|
| CA | 2076018 | 5/2000 |
| CA | 2397655 | 7/2001 |
| CA | 2611324 | 6/2007 |

(Continued)

OTHER PUBLICATIONS

Jin et al. "Enzyme-assisted extraction of lipids directly from the culture of oleaginous yeast *Rhodosporidium toruloides*" (2012), Bioresource Tech, vol. 111: 378-382. (Year: 2012).*
Liang et al. "Enzyme-Assisted Aqueous Extraction of Lipid from Microalgae" (2012), J of AGriculture and Food Chemistry, vol. 60: 11771-11776. (Year: 2012).*
Cooney et al. "Extraction of Bio-oils from Microalgae", (2009), Separation & Purification Reviews, vol. 38(4): 291-325. (Year: 2009).*
Milledge et al. "A review of the harvesting of micro-algae for biofuel production" (2013, pub. online Oct. 2012), Rev. Environ Sci. Biotechnol. vol. 12: 165-178. (Year: 2013).*
"Alternative Methods of Extractions", Oils & Fats International, vol. 6, 1992, pp. 29-32.

(Continued)

*Primary Examiner* — Teresa E Knight
(74) *Attorney, Agent, or Firm* — Kilpatrick Townsend & Stockton LLP (57) ABSTRACT

Provided herein are methods of recovering oil from microorganisms. The methods are useful, for example, in obtaining nutritional oils and/or lipid biofuels. The methods of recovering oil described herein include contacting a population of microorganisms with one or more enzymes under conditions that cause disruption of the microorganisms and extracting lipids from the population of microorganisms in the presence of reduced amounts of organic solvent or in the absence of organic solvent.

19 Claims, 3 Drawing Sheets

(56) References Cited

U.S. PATENT DOCUMENTS

| | | |
|---|---|---|
| 2015/0176042 A1 | 6/2015 | Dennis et al. |
| 2016/0010026 A1 | 1/2016 | Dennis et al. |

FOREIGN PATENT DOCUMENTS

| | | |
|---|---|---|
| CA | 2146235 | 12/2011 |
| CA | 2801011 | 12/2011 |
| CN | 101389749 | 3/2009 |
| CN | 103328620 | 9/2013 |
| DE | 2056896 | 8/1971 |
| DE | 2056896 | 12/1979 |
| EP | 969086 | 1/2000 |
| EP | 1178118 | 2/2002 |
| EP | 1305440 | 6/2010 |
| EP | 1252324 | 10/2010 |
| GB | 808128 | 1/1959 |
| JP | 04211366 | 8/1992 |
| JP | 08509355 | 10/1996 |
| JP | 10072590 | 3/1998 |
| JP | 11116983 | 4/1999 |
| JP | 11285376 | 10/1999 |
| JP | 2000245492 | 9/2000 |
| JP | 2002524406 | 8/2002 |
| WO | 8808025 | 10/1988 |
| WO | 9107498 | 5/1991 |
| WO | 9408467 | 4/1994 |
| WO | 9605278 | 2/1996 |
| WO | 1996021037 | 7/1996 |
| WO | 9704121 | 2/1997 |
| WO | 9736996 | 10/1997 |
| WO | 9737032 | 10/1997 |
| WO | 9803671 | 1/1998 |
| WO | 9850574 | 11/1998 |
| WO | 9932604 | 7/1999 |
| WO | 0153512 | 7/2001 |
| WO | 0210423 | 2/2002 |
| WO | 03092628 | 11/2003 |
| WO | 2011153246 A2 | 12/2011 |
| WO | 2011153246 A3 | 12/2011 |
| WO | 2012062962 | 5/2012 |
| WO | 2012164211 | 12/2012 |
| WO | 2015092546 | 6/2015 |

OTHER PUBLICATIONS

"Pythium", Wkipedia, the free encyclopedia, http://en.wikipedia.org/wiki/Pythium, 2 pages.

U.S. Appl. No. 14/577,471, "Advisory Action", dated Sep. 21, 2016, 4 pages.

U.S. Appl. No. 14/577,471, "Final Office Action", dated Jun. 2, 2016, 17 pages.

U.S. Appl. No. 14/577,471, "Non-Final Office Action", dated Nov. 6, 2015, 15 pages.

U.S. Appl. No. 14/577,471, "Non-Final Office Action", dated Nov. 3, 2016, 16 pages.

U.S. Appl. No. 14/577,471, "Notice of Allowance", dated May 31, 2017, 7 pages.

U.S. Appl. No. 14/862,862, "Final Office Action", dated Jun. 2, 2016, 17 pages.

U.S. Appl. No. 14/862,862, "Non-Final Office Action", dated Nov. 6, 2015, 15 pages.

U.S. Appl. No. 14/862,862, "Non-Final Office Action", dated Sep. 20, 2016, 15 pages.

U.S. Appl. No. 14/862,862, "Notice of Allowance", dated Jun. 1, 2017, 7 pages.

Atkinson et al., "Biochemical engineering and biotechnology handbook", Edition 2, Macmillan Publishers Ltd., 1991, pp. 918-923.

Bennemann et al., "Systems and economic analysis of microalgae ponds for conversion of C02 to biomass", Final Report to the Department of Energy Technology Center,, Mar. 21, 1996, pp. 14-27 & 124-144.

Cartens et al., "Eicosapentaenoic acid (20:5n-3) from the marine microalgaPhaeodactylum tricornutum", Journal of the American Oil Chemists' Society, vol. 73, Issue 8, Aug. 1996, pp. 1025-1031.

Chen et al., "Subcritical co-solvents extraction of lipid from wet microalgae pastes of *Nannochloropsis* sp.", European Journal of Lipid Science and Technology, vol. 114, No. 2, Dec. 16, 2011, pp. 205-212.

Chisti et al., "Disruption of microbial cells for intracellular products", Enzyme Micro b. Technol., vol. 8, Apr. 1986, pp. 194-204.

Enssani et al., "Fundamental parameters in extraction of lipids from wastewater-grown microalgal biomass", Dissertation Thesis, Department of Civil Engineering, University of California, Berkeley, 1987, pp. I-71, 170-174.

EP14871148.4, "Extended European Search Report", dated Oct. 28, 2016, 10 pages.

Hampson et al., "Extraction of lipid-grown bacterial cells by supercritical fluid and organic solvent to obtain pure medium chain-length polyhydroxyalkanoates", Journal of the American Oil Chemists' Society, vol. 76, No. 1, 1999, pp. 1371-1374.

Hruschka et al., "A new oil extraction process: FRIOLEX", Lipids, vol. 5, Issue 5, 1998, pp. 356-360.

Liang et al., "Enzyme-Assisted Aqueous Extraction of Lipid from Microalgae", Journal of Agricultural and Food Chemistry, vol. 60, No. 47, Nov. 28, 2012, pp. 11771-11776.

Lowrey et al., "Nutrient recycling of lipid-extracted waste in the production of an oleaginous thraustochytrid", Applied Microbiology and Biotechnology, Springer, DE, vol. 100, No. 10, Mar. 22, 2016, pp. 4711-4721.

Lowrey et al., "Sequential recycling of enzymatic lipid-extracted hydrolysate in fermentations with a thraustochytrid", Bioresource Technology, vol. 209, Jun. 2016, pp. 333-342.

Medina et al., "Downstream processing of algal polyunsaturated fatty acids", Biotechnology Advances, vol. 16, Issue 3, May 1998, pp. 517-580.

Medina et al., "Lipase-catalyzed esterification of glycerol and polyunsaturated fatty acids from fish and microalgae oils", Journal of Biotechnology, vol. 70, Issue 1-3, Apr. 30, 1999, pp. 379-391.

Middelberg, "Process-scale disruption of microorganisms", Biotechnology Advances, vol. 13, Issue 3, 1995, pp. 491-551.

PCT/IB2014/003113, "International Preliminary Report on Patentability", dated Jun. 30, 2016, 8 pages.

PCT/IB2014/003113, "International Search Report and Written Opinion", dated May 6, 2015, 14 pages.

PCT/IB2014/003136, "International Preliminary Report on Patentability", dated Jun. 30, 2016, 7 pages.

PCT/IB2014/003136, "International Search Report and Written Opinion", dated May 12, 2015, 10 pages.

Pinkart et al., "Rapid separation of microbial lipids using solid phase extraction columns", Journal of Microbiological Methods, vol. 34, Issue 1, Sep. 1, 1998, pp. 9-15.

Ratledge et al., "Down-stream processing, extraction, and purification of single cell oils", Single Cell Oils, Chapter 13, Apr. 2005, pp. 202-219.

Sawayama et al., "Possibility of renewable energy production and CO2 mitigation by thermochemical liquefaction of microalgae", Biomass and Bioenergy, 1999, vol. 17, Issue 1, Jul. 1999, pp. 33-39.

Shimizu et al., "Production of a novel omega-1 eicosapentaenoic add by mortierella-alpina 1 s-4 grown on 1 hexadecene", Archives of Microbiology, vol. 156, No. 3,, 1991, pp. 163-166.

Spellman et al., "Proteinase and exopeptidase hydrolysis of whey protein: Comparison of the TNBS, 77 OPA and pH stat methods for quantification of degree of hydrolysis", International Dairy Journal, vol. 13, Issue 6, 2003, pp. 447-453.

Totani et al., "Industrial Production of Arachidonic Acid by Mortierella", Industrial Application of Single Cell Oils, Chapter 4, 1992, 9 pages.

Wynn et al., "The role of malic enzyme in the regulation of lipid accumulation in filamentous fungi", Microbiology, vol. 145, 1999, pp. 1911-1917.

AU2014369341, "Office Action", dated Dec. 11, 2017, 4 pages.

CN201480067590.8, "Office Action", dated Jul. 25, 2019, 13 pages.

CN201480069710.8, "Office Action", dated Aug. 6, 2019, 4 pages.

MX/A/2016/007643, "Office Action", dated Jun. 21, 2019, 3 pages.

(56) References Cited

OTHER PUBLICATIONS

CN201480069710.8, "Office Action", dated Mar. 4, 2019, 7 pages.
IN201617023108, "First Examination Report", dated Apr. 29, 2019, 5 pages.
JP2016-539098, "Office Action", dated Mar. 26, 2019, 8 pages.
Application No. CA2,934,212, Office Action, dated Apr. 24, 2020, 3 pages.
Application No. EP14843165.3, Office Action, dated May 8, 2020, 6 pages.
Application No. IL245944, Office Action, dated May 26, 2020, 2 pages.
Application No. JP2016-539098, Office Action, dated Jul. 28, 2020, 6 pages.
Application No. JP2019-050054, Office Action, dated Apr. 14, 2020, 10 pages.
Application No. JP2019-135383, Office Action, dated Jul. 21, 2020, 7 pages.
Application No. KR2016-7019552, Office Action, dated Jul. 20, 2020, 8 pages.
Application No. MX/A/2016/008217, Notice of Allowance, dated Aug. 31, 2020, 3 pages.
CA2,933,995, "Office Action", dated Jan. 24, 2020, 3 pages.
IL245941, "Office Action", dated Mar. 4, 2020, 6 pages.
IN201617023109, "First Examination Report", dated Mar. 11, 2020, 6 pages.
MX/A/2016/008217, "Office Action", dated Mar. 2, 2020, 4 pages.
BR1120160142080, "Office Action", dated Nov. 12, 2019, 7 pages.
CN201480067590.8, "Office Action", dated Dec. 13, 2019, 12 pages.
CN201480069710.8, "Office Action", dated Nov. 27, 2019, 4 pages.
EP14843165.3, "Office Action", dated Oct. 15, 2019, 7 pages.
IL245941, "Office Action", dated Oct. 31, 2019, 6 pages.
IL245944, "Office Action", dated Oct. 27, 2019, 6 pages.
MX/A/2016/008217, "Office Action", dated Dec. 13, 2019, 5 pages.
U.S. Appl. No. 15/659,300, "Office Action", dated Sep. 12, 2019, 35 pages.
Application No. BR112016014262-4, Office Action, dated Jan. 5, 2021, 4 pages.
Application No. CA2,934,212, Office Action, dated Nov. 3, 2020, 3 pages.
AU2014369339, "Third Examination Report", dated Sep. 11, 2018, 3 pages.
CN201480067590.8, "Office Action", dated Feb. 20, 2019, 16 pages.
EP14871148.4, "Office Action", dated Dec. 19, 2018, 5 pages.
IL245941, "Office Action", dated Jan. 24, 2019, 7 pages.
IL245944, "Office Action", dated Aug. 30, 2018, 6 pages.
JP2016-539098, "Office Action", dated Oct. 2, 2018, 8 pages.
JP2016-540044, "Office Action", dated Oct. 30, 2018, 6 pages.
AU2014369339, "Second Examination Report", dated Apr. 12, 2018, 4 pages.
EP14871148.4, "Office Action", dated Apr. 26, 2018, 6 pages.
AU2014369339, "First Examination Report", dated Oct. 19, 2017, 5 pages.
EP14871148.4, "Office Action", dated Sep. 6, 2017, 6 pages.

* cited by examiner

METHODS OF RECOVERING OIL FROM MICROORGANISMS

CROSS-REFERENCE TO PRIORITY APPLICATION

This application claims priority to U.S. Provisional Application No. 61/918,880, filed Dec. 20, 2013, which is incorporated herein by reference in its entirety.

BACKGROUND

Oil can be recovered from microorganisms, such as microalgae, using wet extraction methods or dry extraction methods. In dry extraction methods, microorganisms are typically harvested and dried before oil extraction. However, drying is an expensive and energy intensive process. Also, if the oil is rich in polyunsaturated fatty acids (PUFA) (e.g., for food and nutritional supplement applications), the process can cause significant oxidations of the PUFA due to high temperatures involved in drying.

Furthermore, dry extraction methods of recovering oil from microorganisms typically are conducted with organic solvents, such as hexanes, and require coupling with mechanical cell disruption methods for suitable oil yields. However, mechanical disruption methods are expensive and energy intensive, while organic solvents are flammable, toxic, and must be removed from the end oil product.

SUMMARY

Provided herein are methods of recovering oil (i.e., lipids) from microorganisms. The methods are useful, for example, in obtaining nutritional oils and/or lipid biofuels. The methods of recovering oil described herein optionally can be performed as an integrated bioprocess, i.e., as a "one-pot" method.

The methods of recovering lipids from a population of microorganisms described herein comprise contacting the population of microorganisms with one or more enzymes under conditions that cause disruption of the microorganisms and extracting lipids from the disrupted microorganisms in the presence of reduced amounts of organic solvent or in the absence of organic solvent. Optionally, the contacting step occurs in fermentation medium.

The extracting step is optionally performed in the absence of organic solvent. In these examples, at least 60% of lipids can be extracted from the population of microorganisms. The extracting step can optionally be performed using reduced amounts of organic solvent, as compared to traditional extraction methods. In these examples, at least 90% of lipids can be extracted from the population of microorganisms. Optionally, the ratio of microorganisms to organic solvent is from 1:6 to 1:0.2 volume:volume (e.g., 1:0.2 volume:volume). The organic solvent can optionally be hexane.

The population of microorganisms can optionally be concentrated prior to the contacting step. Optionally, the population of microorganisms is concentrated by centrifugation and recovery of the solid phase. The population of microorganisms can be concentrated up to 20% solids (e.g., from 15 to 20% solids).

The contacting step can be performed in the absence of surfactants. Optionally, the contacting step can be performed at a pH between and including 6 to 8.5 (e.g., about 7.5). The contacting step optionally is performed at a temperature between and including 55° C. to 70° C. Optionally, the contacting step can be performed at a temperature of 70° C. or below. The contacting step can be performed for one to twenty hours (e.g., for four hours).

Optionally, the enzyme used in the contacting step is a protease. The enzyme is optionally Alcalase 2.4 L. Optionally, the enzyme is at a concentration of 0.2% to 0.4% volume/volume. The contacting step optionally can be performed in the presence of 0.4% or 0.2% enzyme for eighteen to twenty horns at 55° C. For example, the contacting step can be performed in the presence of 0.4% enzyme for eighteen hours at 55° C. Optionally, the contacting step is performed in the presence of 0.4% enzyme for four to six hours at 70° C.

Optionally, the extracting step is performed in the presence of oil (e.g., coconut oil). Optionally, the extracting step is performed in the presence of biofuel.

Optionally, the method lacks a drying step.

The population of microorganism is selected from the group consisting of algae, fungi, bacteria, and protists. Optionally, the population of microorganisms is selected from the genus *Thraustochytrium, Schizochytrium*, or mixtures thereof. Optionally, the population of microorganisms is a *Thraustochytrium* sp., for example, as deposited as ATCC Accession No. PTA-6245.

The details of one or more embodiments are set forth in the drawings and the description below. Other features, objects, and advantages will be apparent from the description and drawings, and from the claims.

DETAILED DESCRIPTION

Described herein are methods of recovering lipids from a population of microorganisms. The methods of recovering lipids include contacting the population of microorganisms with one or more enzymes under conditions that cause disruption of the microorganisms and extracting lipids from the disrupted microorganisms in the presence of reduced amounts of organic solvent or in the absence of organic solvent. The method described herein can be referred to as a "one-pot" or "integrated" process because the microbial oil production and cell disruption to release the oil optionally can be performed within the same vessel. Therefore, the downstream processing steps (e.g., oil extraction and recovery) can be integrated at the end of the upstream processing steps (e.g., fermentation).

I. Microorganisms

The methods described herein include recovering lipids from a population of microorganisms. The population of microorganisms described herein can be algae (e.g., microalgae), fungi (including yeast), bacteria, or protists. Optionally, the microorganism includes Tharustochytrids of the order Thraustochytriales, more specifically Thraustochytriales of the genus *Thraustochytrium* and *Schizochytrium*. Optionally, the population of microorganisms includes Thraustochytriales as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18).

The microorganisms for use in the methods described herein can produce a variety of lipid compounds. As used herein, the term lipid includes phospholipids, free fatty acids, esters of fatty acids, triacylglycerols, sterols and sterol esters, carotenoids, xanthophyls (e.g., oxycarotenoids), hydrocarbons, and other lipids known to one of ordinary skill in the art. Optionally, the lipid compounds include unsaturated lipids. The unsaturated lipids can include poly-unsaturated lipids (i.e., lipids containing at least 2 unsaturated carbon-carbon bonds, e.g., double bonds) or highly unsaturated lipids (i.e., lipids containing 4 or more unsaturated carbon-carbon bonds). Examples of unsaturated lipids include omega-3 and/or omega-6 polyunsaturated fatty acids, such as docosahexaenoic acid (i.e., DHA), eicosapentaenoic acid (i.e., EPA), and other naturally occurring unsaturated, polyunsaturated and highly unsaturated compounds.

II. Process

Fermentation

The microorganisms described herein can be cultured according to methods known in the art. For example, a Thraustochytrid, e.g., a *Thraustochytrium* sp., can be cultivated according to methods described in U.S. Patent Publication US 2009/0117194 or US 2012/0244584, which are herein incorporated by reference in their entireties. Microorganisms are grown in a growth medium (also known as "culture medium"). Any of a variety of media can be suitable for use in culturing the microorganisms described herein. Optionally, the medium supplies various nutritional components, including a carbon source and a nitrogen source, for the microorganism.

Optionally, the microorganisms provided herein are cultivated under conditions that increase biomass and/or production of a compound of interest (e.g., oil or total fatty acid (TFA) content). Thraustochytrids, for example, are typically cultured in saline media. Optionally, Thraustochytrids can be cultured in medium having a salt concentration from about 2.0 g/L to about 50.0 g/L. Optionally. Thraustochytrids are cultured in media having a salt concentration from about 2 g/L to about 35 g/L (e.g., from about 18 g/L to about 35 g/L). Optionally, the Thraustochytrids described herein can be grown in low salt conditions. For example, the Thraustochytrids can be cultured in a medium having a salt concentration from about 5 g/L to about 20 g/L (e.g., from about 5 g/L to about 15 g/L). The culture media optionally include NaCl. Optionally, the media include natural or artificial sea salt and/or artificial seawater.

The chloride concentration in culture media can be reduced (i.e., lower in amount) as compared to traditional methods. The culture media can include non-chloride-containing sodium salts (e.g., sodium sulfate) as a source of sodium. For example, a significant portion of the total sodium can be supplied by non-chloride salts such that less than about 100%, 75%, 50%, or 25% of the total sodium in culture media is supplied by sodium chloride.

Optionally, the culture media have chloride concentrations of less than about 3 g/L, 500 mg/L, 250 mg/L, or 120 mg/L. For example, culture media have chloride concentrations of between and including about 60 mg/L and 120 mg/L. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein.

Media for Thraustochytrid culture can include any of a variety of carbon sources. Examples of carbon sources include fatty acids; lipids; glycerols; triglycerols; carbohydrates such as glucose, starch, celluloses, hemicelluloses, fructose, dextrose, xylose, lactulose, galactose, maltotriose, maltose, lactose, glycogen, gelatin, starch (corn or wheat), acetate, m-inositol (derived from corn steep liquor), galacturonic acid (derived from pectin), L-fucose (derived from galactose), gentiobiose, glucosamine, alpha-D-glucose-1-phosphate (derived from glucose), cellobiose, dextrin, and alpha-cyclodextrin (derived from starch); sucrose (from molasses); polyols such as maltitol, erythritol, adonitol and oleic acids such as glycerol and tween 80; amino sugars such as N-acetyl-D-galactosamine, N-acetyl-D-glucosamine and N-acetyl-beta-D-mannosamine; and any kind of biomass or waste stream.

Optionally, media include carbon sources at a concentration of about 5 g/L to about 200 g/L. Media can have a C:N (carbon to nitrogen) ratio between about 1:1 and about 40:1. When two-phase cultures are used, media can have a C:N ratio of between and including about 1:1 to about 5:1 for the first phase, then about 1:1 to about 1:~0 (i.e., no or minimal nitrogen) in the second phase. As used herein, the term minimal refers to less than about 10% (e.g., less than about 9%, less than about 8%, less than about 7%, less than about 6%, less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1%). For example, minimal nitrogen in media can refer to less than about 10% (e.g., less than about 9%, less than about 8%, less than about 7.%, less than about 6%, less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1%) of nitrogen in the media.

Media for Thraustochytrids culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable media typically range between and including about 1 g/L and about 25 g/L.

The media optionally include a phosphate, such as potassium phosphate or sodium-phosphate. Inorganic salts and trace nutrients in media can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium is adjusted to a pH from 4.0 to 6.5, inclusively. The medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Cells can be cultivated for anywhere from 1 day to 60 days. Optionally, cultivation is carried out for 14 days or less, 13 days or less, 12 days or less, 11 days or less, 10 days or less, 9 days or less, 8 days or less, 7 days or less, 6 days or less, 5 days or less, 4 days or less, 3 days or less, 2 days or less, or 1 day or less. Cultivation is optionally carried out at temperatures from about 4° C. to about 30° C., e.g., from about 18° C. to about 28° C. Cultivation can include aeration-shaking culture, shaking culture, stationary culture, batch culture, semi-continuous culture, continuous culture, rolling batch culture, wave culture, or the like. Cultivation can be performed using a conventional agitation-fermenter, a bubble column fermenter (batch or continuous cultures), a wave fermenter, etc.

Cultures can be aerated by one or more of a variety of methods, including shaking. Optionally, shaking ranges from about 100 rpm to about 1000 rpm, e.g., from about 350 rpm to about 600 rpm or from about 100 to about 450 rpm. Optionally, the cultures are aerated using different shaking speeds during biomass-producing phases and during lipid-producing phases. Alternatively or additionally, shaking speeds can vary depending on the type of culture vessel (e.g., shape or size of flask).

Optionally, the level of dissolved oxygen (DO) is higher during the biomass production phase than it is during the lipid production phase. Thus, DO levels are reduced during the lipid production phase (i.e., the DO levels are less than the amount of dissolved oxygen in biomass production phase). Optionally, the level of dissolved oxygen is reduced below saturation. For example, the level of dissolved oxygen can be reduced to a very low, or even undetectable, level.

The production of desirable lipids can be enhanced by culturing cells according to methods that involve a shift of one or more culture conditions in order to obtain higher quantities of desirable compounds. Optionally, cells are cultured first under conditions that maximize biomass, followed by a shift of one or more culture conditions to conditions that favor lipid productivity. Conditions that are shifted can include oxygen concentration, C:N ratio, temperature, and combinations thereof. Optionally, a two-stage culture is performed in which a first stage favors biomass production (e.g., using conditions of high oxygen (e.g., generally or relative to the second stage), low C:N ratio, and ambient temperature), followed by a second stage that favors lipid production (e.g., in which oxygen is decreased, C:N ratio is increased, and temperature is decreased).

Pasteurization

Optionally, the resulting biomass is pasteurized to kill the cells and inactivate undesirable substances present in the biomass. For example, the biomass can be pasteurized to inactivate compound degrading substances. The biomass can be present in the fermentation media or isolated from the fermentation media for the pasteurization step. The pasteurization step can be performed by heating the biomass and/or fermentation media to an elevated temperature. For example, the biomass and/or fermentation media can be heated to a temperature from about and including 50° C. to about and including 95° C. (e.g., from about and including 60° C. to about and including 90° C. or from about and including 65° C. to about and including 80° C.). Optionally, the biomass and/or fermentation media can be heated from about and including 30 minutes to about and including 120 minutes (e.g., from about and including 45 minutes to about and including 90 minutes, or from about and including 55 minutes to about and including 75 minutes). The pasteurization can be performed using a suitable heating means as known to those of skill in the art, such as by direct steam injection.

Harvesting and Washing

Optionally, the biomass can be harvested according to methods known to those of skill in the art. For example, the biomass can optionally be collected from the fermentation media using various conventional methods, such as centrifugation (e.g., solid-ejecting centrifuges) or filtration (e.g., cross-flow filtration) and can also include the use of a precipitation agent for the accelerated collection of cellular biomass (e.g., sodium phosphate or calcium chloride).

Optionally, the biomass is washed with water. Optionally, the biomass can be concentrated up to about and including 20% solids. For example, the biomass can be concentrated to about and including 5% to about and including 20% solids, from about and including 7.5% to about and including 15% solids, or from about and including 15% solids to about and including 20% solids, or any percentage within the recited ranges. Optionally, the biomass can be concentrated to about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

Hydrolysis

Cell hydrolysis (i.e., cell disruption) can be performed using chemical, enzymatic, and/or mechanical methods. Chemical methods for hydrolyzing the cells can include adding acid to the cells, which is referred to herein as acid hydrolysis. In the acid hydrolysis method, the biomass can be washed with water using, for example, centrifugation, and concentrated as described above prior to hydrolyzing the cells. Optionally, the biomass is concentrated to about 15% solids with water.

Acid is then added to the washed, wet biomass. Optionally, the biomass is not dried prior to adding the acid. Suitable acids for use in the acid hydrolysis step include sulfuric acid, hydrochloric acid, phosphoric acid, hydrobromic acid, nitric acid, perchloric acid, and other strong acids as known to those of skill in the art. A suitable amount of acid can added to the washed, wet biomass to achieve a final concentration of from about and including 100 mM to about and including 200 mM (e.g., from about and including 120 mM to about and including 180 mM or from about and including 140 mM to about and including 160 mM). Sulfuric acid can be added to the washed, wet biomass to a final concentration of 160 mM.

The resulting mixture including water, biomass, and acid can then be incubated for a period of time to hydrolyze the cells. Optionally, the mixture can be incubated at a temperature of from about and including 30° C. to about and including 200° C. For example, the mixture can be incubated at a temperature of from about and including 45° C. to about and including 180° C., from about and including 60° C. to about and including 150° C., or from about and including 80° C. to about and including 130° C. Optionally, the mixture is incubated in an autoclave at a temperature of 121° C. The mixture can be incubated for a period of time suitable to hydrolyze at least 50% of the cells (e.g., at least 60% of the cells, at least 70% of the cells, at least 80% of the cells, at least 90% of the cells, at least 95% of the cells, or 100% of the cells). The period of time for incubating the cells depends on the incubation temperature. Incubating the mixture at a higher temperature can result in the hydrolysis proceeding at a faster rate (i.e., requiring a shorter period of time for hydrolysis). In some examples, the cells can be incubated at 60° C. for 1 hour. Optionally, the incubation step is performed using direct or indirect pasteurization equipment, such as, for example, a continuous flow thermal system commercially available from Microthermics (e.g., MicroThermics UHT/HTST Lab 25 EHV Hybrid) (Raleigh, N.C.).

As described above, cell hydrolysis (i.e., cell disruption) can be performed using enzymatic methods. Specifically, the population of microorganisms can be contacted with one or more enzymes under conditions that cause disruption of the microorganisms. Optionally, the enzyme is a protease. An example of a suitable protease is ALCALASE 2.4 L FG (Novozymes; Franklinton, N.C.). Optionally, the cells are not washed with water prior to the enzymatic hydrolysis.

The population of microorganisms can be fermented to float in aqueous media. The fermentation media can be gravity settled in the fermenter and the media can be decanted or otherwise removed to provide the desired concentration of the population of microorganisms. Alternatively, the fermentation media can be concentrated by centrifugation to provide the desired concentration of the population of microorganisms. The population of microorganisms can be concentrated to up to and including 20% solids. For example, the population of microorganisms can be concentrated from about and including 5% to about and including 20% solids, from about and including 7.5% to about and including 15% solids, or from about and including 15% solids to about and including 20% solids, or any percentage within the recited ranges. The population of microorganisms can be concentrated prior to contacting the microorganisms with the one or more enzymes.

Prior to contacting the microorganisms with the one or more enzymes, the pH of the fermentation media can optionally be adjusted to from about and including 6 to 8.5, e.g., from about and including 6.5 to 8.5 or from about and including 7 to 8, or any value within the recited ranges. For example, the pH of the fermentation media can optionally be adjusted to 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, or 8.5. The pH can be adjusted using, for example, a base such as sodium hydroxide (e.g., 1N NaOH), ammonium hydroxide, calcium hydroxide, magnesium hydroxide, or potassium hydroxide.

The microorganisms can be contacted with the one or more enzymes while the population of microorganisms is in the fermentation medium (i.e., the contacting step occurs in the fermentation medium). Optionally, the enzyme added to the fermentation medium is at a concentration of from about 0.2% to about 0.4% volume/volume (v/v). For example, the enzyme added to the fermentation medium can be at a concentration of from 0.2% (v/v) 0.25% (v/v), 0.30% (v/v), 0.35% (v/v), or 0.4% (v/v).

The contacting step can be performed at a temperature of 70° C. or below. For example, the microorganisms can be contacted with the one or more enzymes at a temperature of about 70° C. or below, about 65° C. or below, about 60° C. or below, about 55° C. or below, about 50° C. or below, or about 45° C. or below. Optionally, the contacting step is performed at a temperature of from about and including 45° C. to about and including 70° C., from about and including 50° C. to about and including 70° C., or from about and including 55° C. to about and including 65° C. The contacting step can be performed for a suitable period of time to result in the disruption of the microorganisms. For example, the contacting step can be performed from about and including 1 hour to about and including 20 hours, e.g., from 2 hours to 18 hours, from 4 hours to 16 hours, from 6 hours to 14 hours, or from 8 hours to 12 hours, or any timeframe within the recited ranges. Optionally, the contacting step can be performed for about four hours and the hydrolysis temperature can optionally be about 70° C.

Optimum temperature, time, pH, and enzyme concentration depend on the specific enzyme, and a person of ordinary skill in the art would be able to modify the temperature, time, pH, and enzyme concentration as appropriate for a given enzyme.

Optionally, the contacting step is performed in the presence of either about 0.2% or about 0.4% enzyme for about 18 to 20 hours at about 55° C. For example, the contacting step can be performed in the presence of 0.4% enzyme for eighteen hours at 55° C. Alternatively, the contacting step is performed in the presence of 0.4% enzyme for four to six hours at 70° C. Optionally, the contacting step is performed in the absence of surfactants (i.e., no surfactant is present).

Optionally, the cell disruption can be performed using other chemical and mechanical methods as known to those of skill in the art. For example, cell disruption can be performed using alkaline hydrolysis, bead milling, sonication, detergent hydrolysis, solvent extraction, rapid decompression (i.e., the cell bomb method), or high-shear mechanical methods, contact with a chemical, homogenization, ultrasound, milling, shear forces. French press, cold-pressing, heating, drying, osmotic shock, pressure oscillation, expression of an autolysis gene, or combinations of these. Optionally, the cell disruption can be performed using a combination of two or more of the chemical, enzymatic, and/or mechanical methods described herein (e.g., enzymatic hydrolysis in combination with bead-milling). The cell disruption methods can be performed sequentially (e.g., bead-milling followed by enzymatic hydrolysis).

Extraction

As described above, lipids are extracted from the population of microorganisms in the presence of reduced amounts of organic solvent (i.e., organic solvent extraction) or in the absence of organic solvent.

Optionally, the extraction step is performed using reduced amounts of organic solvent as compared to the amounts of organic solvents needed to extract lipids from whole dry microbial cells. As used herein, the term reduced amounts of organic solvent compared to the amounts of organic solvent needed to extract lipids from whole dry microbial cells means an amount of organic solvent less than that needed to extract lipids from whole dry microbial cells. For example, the ratio of microorganisms or biomass to organic solvent needed for whole dry microbial cells is typically 1:4 or greater. Thus, the reduced amount of organic solvent can provide a ratio of microorganisms or biomass to organic solvent of less than about 1:4. For example, the ratio of microorganisms or biomass to organic solvent for extracting oil from the hydrolyzed wet biomass described herein can be from about and including 1:0.2 to about and including 1:1 (e.g., 1:0.2, 1:0.3, 1:0.4, 1:0.5, 1:0.6, 1:0.7, 1:0.8, or 1:0.9). Optionally, additional amounts of organic solvent can be used, such as up to about a 1:6 ratio of microorganisms or biomass to organic solvent.

Suitable organic solvents for use in the extraction step include hexane, isopropyl alcohol, methylene chloride, dodecane, methanol, ethylated oil, and supercritical carbon dioxide.

The organic solvent and microorganisms or biomass can be mixed for a period of time suitable to extract lipids from the microorganisms or biomass. For example, the organic solvent and microorganisms or biomass can be mixed for about 10 minutes or more, 20 minutes or more, 30 minutes or more, 40 minutes or more, 50 minutes or more, 1 hour or more, or 2 hours or more. Subsequently, the lipid can be separated from the remaining components of the mixture by centrifuging the solution.

Optionally, at least about 50% of the lipids theoretically produced by the microorganisms are extracted from the population of microorganisms using this method (i.e., the method provides at least a 50% yield). For example, the yields of lipids extracted from the population of microorganisms can be at least 600%, at least 70%, at least 80%, or at least 90%.

Lipids can also be extracted from the population of microorganisms in the absence of organic solvent. As used herein, in the absence of organic solvent means less than about 0.5% organic solvent based on the weight of the population of microorganisms (e.g., less than about 0.4%, less than about 0.3%, less than about 0.2%, less than about 0.1%, less than about 0.05%, less than about 0.01%, less than about 0.005%, or 0%).

Optionally, the lipids can be extracted from the disrupted microorganisms by using oil (e.g., coconut oil) or biofuel.

Optionally, the oil added during the extraction step can be a nutritional oil (e.g., an oil derived or obtained from a nutritional source). Examples of suitable nutritional oils for use in the methods described herein include coconut oil, palm oil, canola oil, sunflower oil, soy oil, corn oil, olive oil, safflower oil, palm kernel oil, cottonseed oil, and combinations thereof. Derivatives of any of those oils, such as alkylated derivatives (e.g., methylated or ethylated oils), also could be used.

As used herein, biofuel refers to any fuel, fuel additive, aromatic, and/or aliphatic compound derived from a biomass starting material. For example, suitable biofuels for use in the methods described herein can be derived from plant sources or algal sources. Examples of suitable sources for biofuel include algae, corn, switchgrass, sugarcane, sugarbeet, rapeseed, soybeans, and the like.

Optionally, biofuels can be obtained by harvesting oils from a biological source and converting the oils into biofuel. Methods of converting oils obtained from biological sources (e.g., oils obtained from plant and/or algal sources) are known to those of skill in the art. Optionally, the methods of obtaining biofuels can include cultivating an oil-producing biomass (e.g., algae), extracting the oil (e.g., algal oil), and converting the oil (e.g., algal oil) to form a biofuel. Optionally, the oil can be converted to a biofuel using transesterification. As used herein, transesterification refers to a process of exchanging an alkoxy group of an ester by another alcohol. For example, a transesterification process for use in the methods described herein can include converting algal oil, e.g., triglycerides, to biodiesel, e.g., fatty acid alkyl esters, and glycerol. Transesterification can be accomplished by using traditional chemical processes such as acid or base catalyzed reactions, or by using enzyme-catalyzed reactions.

As used herein, the term organic solvents does not include biofuels, as that term is defined herein, and does not include nutritional oils, such as coconut oil, palm oil, canola oil, sunflower oil, soy oil, corn oil, olive oil, safflower oil, palm kernel oil, cottonseed oil or alkylated (e.g., methylated or ethylated) derivatives thereof.

Optionally the oil or biofuel used to extract lipids from the disrupted microorganisms is not subsequently removed from the extracted lipids. A subsequent fractionation of the extracted oil, wherein the added oil or biofuel stays with only one of the oil fractions, is not considered removal of the oil or biofuel from the extracted lipid. For example, after recovery the oils described herein may be combined with other oils for use as, or incorporated into, one or more of the products described herein. Any one of those other oils or products, such as a biofuel, may be added to the mixture of lipids and biomass during the extraction step as an alternative to, or in addition to, combining with the recovered oil after the conclusion of the recovery process. Adding the other oil during the extraction step can assist demulsification and separation of the lipid from the spent biomass.

In traditional methods that rely on organic solvent extraction to separate lipid from biomass, the organic solvent must be removed from the lipids after recovery, although typically at least trace amounts of solvent are left behind. In the methods described herein, however, optionally more than about 80% of the oil or biofuel added during the extraction step remains in the recovered oil when it is used as, or incorporation into, a final product. That is, optionally less than about 20% of the oil or biofuel added during the extraction step is removed from the recovered oil prior to its use as, or incorporation into, a final product. For example, optionally less than about 15%, less than about 10%, less than about 5%, less than about 2%, or 0% of the oil or biofuel added during the extraction step is removed from the recovered oil prior to its use as, or incorporation into, a final product.

Optionally, at least 40% of the lipids theoretically produced by the microorganisms are extracted from the population of microorganisms using this method (i.e., the method provides at least about a 40% yield). For example, the yields of lipids extracted from the population of microorganisms can be at least about 50%, at least 60%, at least 70%, or at least 80%.

Alternatively, the lipids can be extracted using mechanical methods. The hydrolyzed biomass and microorganisms can be centrifuged and the lipids can be separated from the remainder of the components. Optionally, the lipids are contained in the upper layer of the centrifuged material and can be removed by suction or decanting, for example, from the other material.

III. Products

Polyunsaturated fatty acids (PUFAs) and other lipids produced according to the method described herein can be utilized in any of a variety of applications, for example, exploiting their biological or nutritional properties. Optionally, the compounds can be used in pharmaceuticals, food supplements, animal feed additives, cosmetics, and the like. Lipids produced according to the methods described herein can also be used as intermediates in the production of other compounds.

Optionally, the lipids produced according to the methods described herein can be incorporated into a final product (e.g., a food or feed supplement, an infant formula, a pharmaceutical, a fuel, etc.) Suitable food or feed supplements for incorporating the lipids described herein into include beverages such as milk, water, sports drinks, energy drinks, teas, and juices; confections such as jellies and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods and the like; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFA) can be incorporated into a pharmaceutical. Examples of such pharmaceuticals include various types of tablets, capsules, drinkable agents, etc. Optionally, the pharmaceutical is suitable for topical application. Dosage forms can include, for example, capsules, oils, granula, granula subtilae, pulveres, tabellae, pilulae, trochisci, or the like.

The lipids produced according to the methods described herein can be incorporated into products as described herein by combinations with any of a variety of agents. For instance, such compounds can be combined with one or more binders or fillers. In some embodiments, products can include one or more chelating agents, pigments, salts, surfactants, moisturizers, viscosity modifiers, thickeners, emollients, fragrances, preservatives, etc., and combinations thereof.

The examples below are intended to further illustrate certain aspects of the methods and compositions described herein, and are not intended to limit the scope of the claims.

EXAMPLES

Example 1. Pasteurization, Harvesting and Washing, and Chemical Hydrolysis

Pasteurization

T18 biomass was heated with stirring at 60° C. for 1 hour to pasteurize the cells.

Harvesting and Washing

Pasteurized T18 biomass was centrifuged at 4150 rpm for 20 minutes at ambient temperature to separate the final media from the cell paste. The media was removed, and an equivalent mass of water was added to the cell paste to wash the cells. The cell paste-water mixture was shaken for 1 minute, re-centrifuged, and the aqueous phase was removed.

Chemical Hydrolysis

Figure 1:
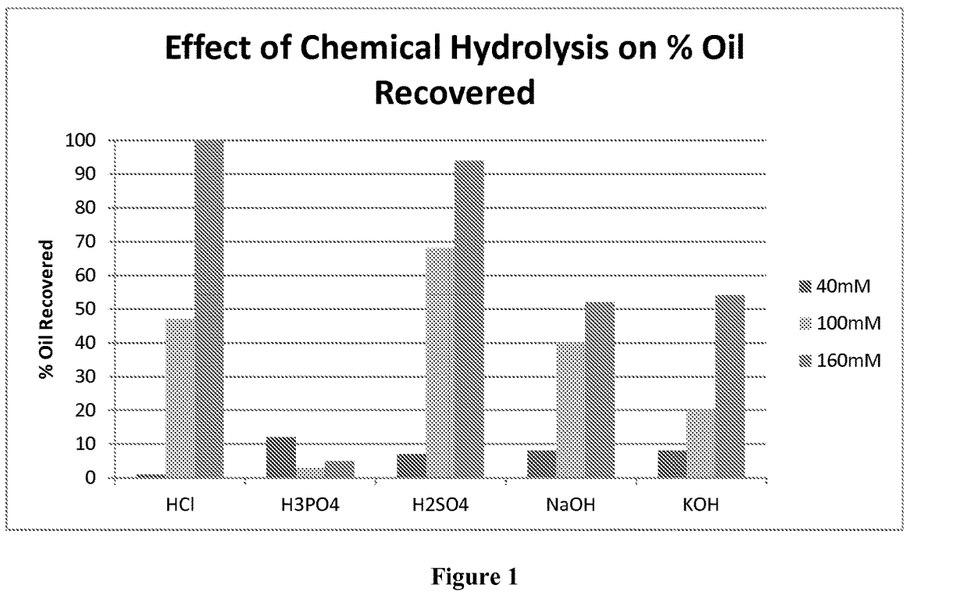
FIG. 1 is a graph showing the percentage of oil recovered from cells hydrolyzed with 40 mM (left bar), 100 mM (middle bar), and 160 mM (right bar) of hydrochloric acid, phosphoric acid, sulfuric acid, sodium hydroxide, and potassium hydroxide.

The water-washed T18 cell paste was adjusted to 150 g/L with water. Subsamples (10 mL) were removed and added to 50 mL centrifuge tubes. Each subsample was treated with acid or base to a final concentration according to Table 1. The mixtures were autoclaved at 121° C. for 15 minutes to hydrolyze the cells. After hydrolysis, the samples were hexane-extracted to determine the percentage of oil recovered by mass balance (FIG. 1). Hydrolysis with 160 mM HCl and $H_2SO_4$ resulted in oil recoveries of greater than 85%.

TABLE 1

| Sample Number | Acid/Base Type | Concentration (mM) | Oil Recovery (%) |
|---|---|---|---|
| 1 | HCl | 40 | 1 |
| 2 | HCl | 100 | 47 |
| 3 | HCl | 160 | 100 |
| 4 | $H_3PO_4$ | 40 | 12 |
| 5 | $H_3PO_4$ | 100 | 3 |
| 6 | $H_3PO_4$ | 160 | 5 |
| 7 | $H_2SO_4$ | 40 | 7 |
| 8 | $H_2SO_4$ | 100 | 68 |
| 9 | $H_2SO_4$ | 160 | 94 |
| 10 | NaOH | 40 | 8 |
| 11 | NaOH | 100 | 40 |
| 12 | NaOH | 160 | 52 |
| 13 | KOH | 40 | 8 |
| 14 | KOH | 100 | 20 |
| 15 | KOH | 160 | 54 |

Example 2. Enzymatic Hydrolysis

Figure 2:
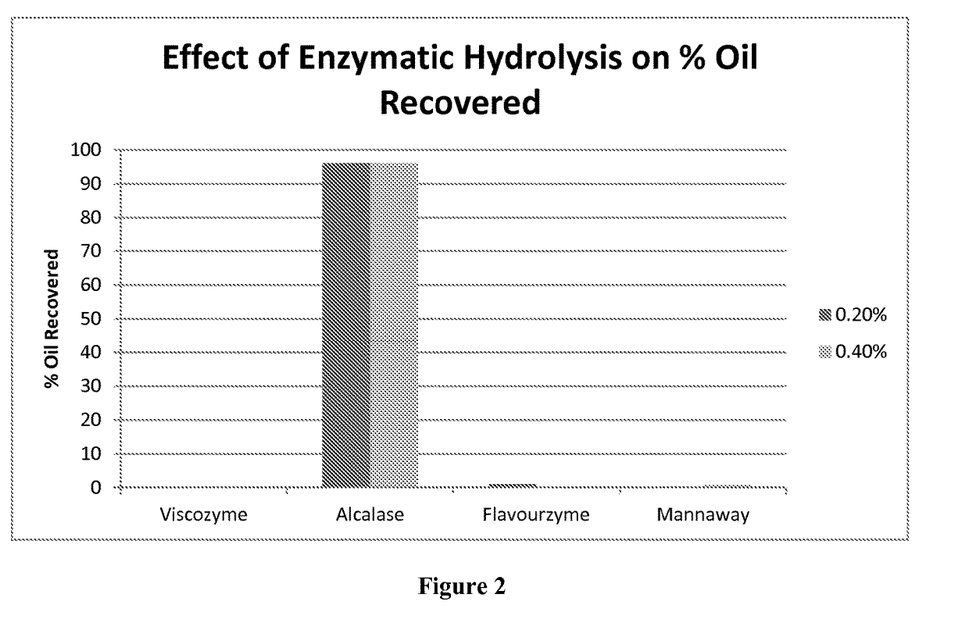
FIG. 2 is a graph showing the percentage of oil recovered from cells enzymatically hydrolyzed with 0.2% (left bar) and 0.4% (right bar) of Viscozyme, Alcalase, Flavourzyme, and Mannaway enzymes.

A water-washed T18 cell paste was adjusted to 220 g/L with water. The pH was adjusted to 7.5 with 1N NaOH. Subsamples (10 mL) were removed and added to 50 mL centrifuge tubes. Each subsample was treated with enzyme according to Table 2. The mixtures were incubated with shaking at 50° C. for 22 hours to hydrolyze the cells. After hydrolysis, the samples were hexane-extracted to determine the percentage of oil recovered by mass balance (FIG. 2). Hydrolysis with Alcalase alone or in combination with another enzyme resulted in oil recoveries of greater than 85%.

TABLE 2

| Sample Number | Enzyme | Concentration (% v/v) | Oil Recovery (%) |
|---|---|---|---|
| 1 | Viscozyme | 0.2 | 0.1 |
| 2 |  | 0.4 | 0.3 |
| 3 | Alcalase | 0.2 | 96 |
| 4 |  | 0.4 | 96 |
| 5 | Flavourzyme | 0.2 | 1 |
| 6 |  | 0.4 | 0.3 |
| 7 | Mannaway | 0.2 | 0 |
| 8 |  | 0.4 | 0.8 |
| 9 | Alcalase/Viscozyme | 0.2/0.2 | 93 |
| 10 | Alcalase/Mannaway | 0.2/0.2 | 91 |
| 11 | Flavourzyme/Mannaway | 0.2/0.2 | 0.3 |

Example 3. Acid and Enzymatic Hydrolysis, Effect of Washing

Figure 3:
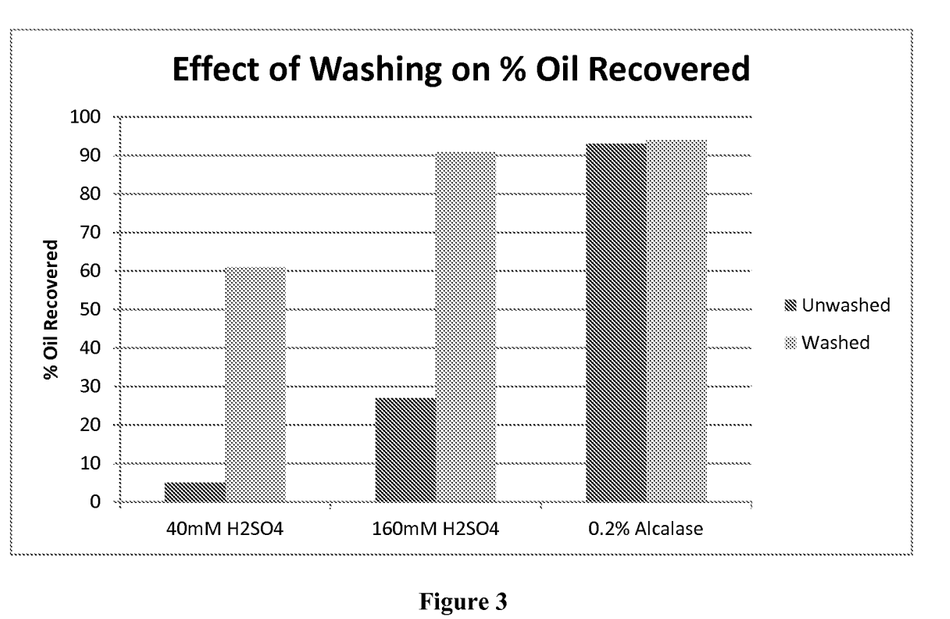
FIG. 3 is a graph showing the percentage of oil recovered from cells not washed (left bar) and washed (right bar) after hydrolysis with 40 mM $H_2SO_4$, 160 mM $H_2SO_4$, and 0.2% Alcalase.

Subsamples of pasteurized, nonwashed T18 biomass (10 mL) were added to 50 mL centrifuge tubes. The controls were water-washed, adjusted to 170 g/L water, and sub-sampled into 50 mL centrifuge tubes. Each subsample was treated with acid or enzyme according to Table 3. The acid hydrolyzed samples were autoclaved at 121° C. for 15 minutes to hydrolyze the cells. The enzymatically hydrolyzed samples were adjusted to pH 7.5 with 1N NaOH and incubated with shaking at 50° C. for 26 hours to hydrolyze the cells. After acid or enzymatic hydrolysis, the samples were hexane-extracted to determine the percentage of oil recovered by mass balance (FIG. 3). Non-washed oil recoveries equivalent to washed oil recoveries were achieved with 0.2% Alcalase hydrolysis.

TABLE 3

| Sample Number | Washed/Not Washed | Acid/Enzyme Treatment | Concentration | Oil Recovered (%) |
|---|---|---|---|---|
| 1 | Not Washed | $H_2SO_4$ | 40 mM | 5 |
| 2 | Washed | $H_2SO_4$ | 40 mM | 61 |
| 3 | Not Washed | $H_2SO_4$ | 160 mM | 27 |
| 4 | Washed | $H_2SO_4$ | 160 mM | 91 |
| 5 | Not Washed | Alcalase | 0.2% v/v | 93 |
| 6 | Washed | Alcalase | 0.2% v/v | 94 |

Example 4. Enzymatic Hydrolysis, Effect of Temperature/Time

Figure 4:
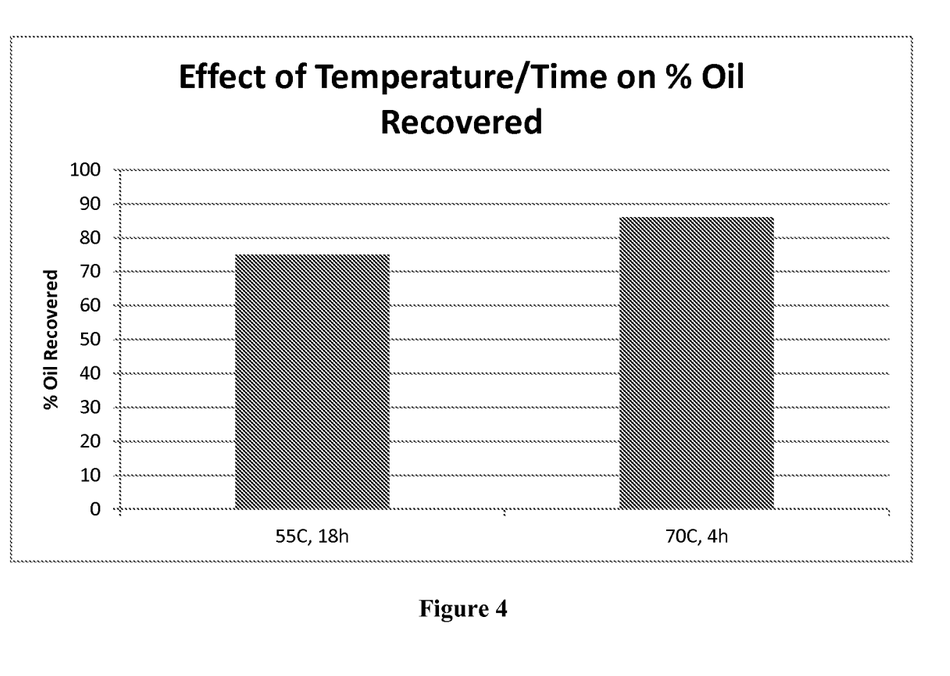
FIG. 4 is a graph showing the percentage of oil recovered from cells enzymatically hydrolyzed at 55° C. for 18 hours and at 70° C. for 4 hours.

The water-washed T18 cell paste was adjusted to 210 g/L with water. The pH was adjusted to 7.5 with 1N NaOH. Subsamples (10 mL) were added into 50 mL centrifuge tubes. Each subsample was treated with 0.2% v/v Alcalase. The mixtures were incubated with shaking at 70° C. for 4 hours to hydrolyze the cells. The controls were incubated with shaking at 55° C. for 18 hours. After hydrolysis, the samples were hexane-extracted to determine the percentage of oil recovered by mass balance (FIG. 4). By increasing the temperature to 70° C., oil recoveries equivalent to hydrolyzing at 55° C. for 18 hours were achieved in 4 hours.

Example 5. Enzymatic Hydrolysis, Extraction with Reduced Organic Solvent

Figure 5:
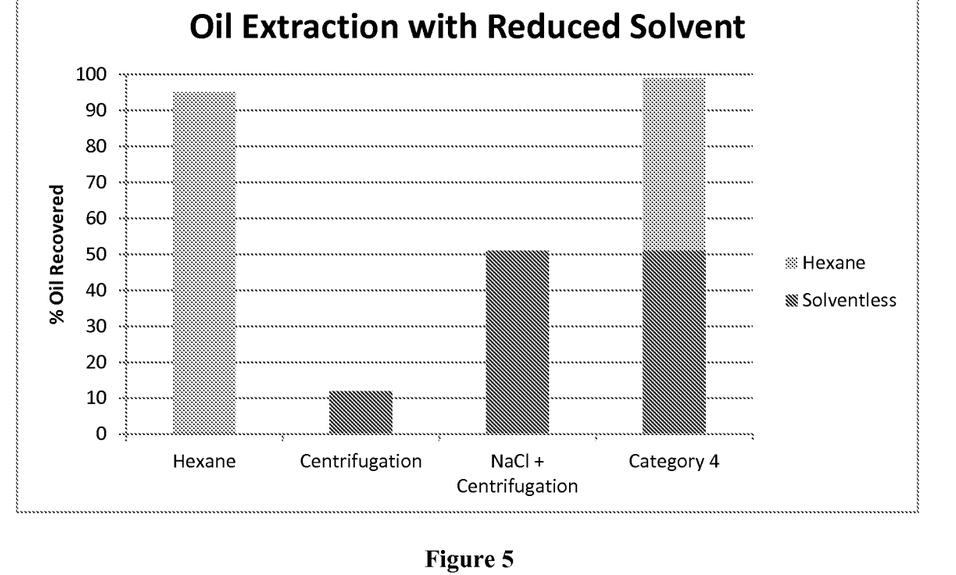
FIG. 5 is a graph showing the percentage of oil recovered from cells enzymatically hydrolyzed and extracted with organic solvent, with reduced amounts of organic solvent, and with no organic solvent.

The water-washed T18 cell paste was adjusted to 220 g/L with water. The pH was adjusted to 7.5 with 1N NaOH. Subsamples (10 mL) were added to 50 mL centrifuge tubes. Each subsample was treated with 0.2% v/v Alcalase. The mixtures were incubated with shaking at 55° C. for 22 hours to hydrolyze the cells. After hydrolysis, each subsample was extracted according to Table 4 and the percentage of oil recovered was determined by mass balance (FIG. 5). The control was hexane extracted with 1:2 (wet biomass:hexane). Sample 2 was centrifuged at 4150 rpm for 20 minutes at 40° C. Sample 3 was treated with 20 g/L NaCl followed by centrifugation. Sample 4 was treated with 20 g/L NaCl followed by centrifugation. The oil layer was removed and 1:0.2 (wet biomass:hexane) was added to extract the remaining oil. By removing the free oil before hexane extraction, oil recoveries equivalent to a 1:2 (wet biomass:hexane) ratio were achieved with a 1:0.2 (wet biomass:hexane) ratio.

TABLE 4

| Sample Number | Extraction Method | Oil Recovered (%) |
|---|---|---|
| 1 | 1:2 wet biomass:hexane | 95 |
| 2 | Solventless (Centrifugtion Alone) | 12 |
| 3 | 20 g/L NaCl + Centrifugation | 51 |
| 4 | NaCl + Centrifugation > 1:0.2 wet biomass:hexane | 99 |

Example 6. Enzymatic Hydrolysis, Extraction with Biofuel

Figure 6:
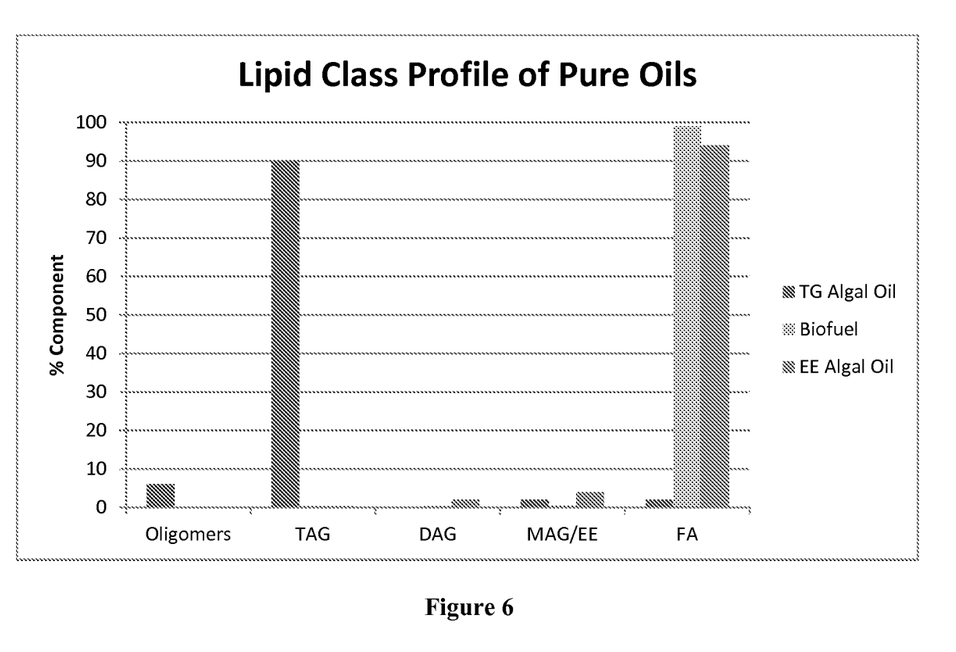
FIG. 6 is a graph showing the percentage of oil recovered from cells enzymatically hydrolyzed and extracted with biofuel based on the lipid class profile of the pure oils, including triglyceride (TG) algal oil (left bar), biofuel (middle bar), and ethylated (EE) algal oil (right bar).

The water-washed T18 cell paste was adjusted to 200 g/L with water, and the pH was adjusted to 7.5 with 1N NaOH. Subsamples (10 mL) were removed and added to 50 mL centrifuge tubes. Each subsample was treated with 0.2% v/v Alcalase. The mixtures were incubated with shaking at 55° C. for 18 hours to hydrolyze the cells. After hydrolysis, each subsample was extracted with biofuel according to Table 5 and the percentage of oil was determined by mass balance and based on the lipid class profile of the pure oils (FIG. 6 and Table 5). Extraction with 1:0.4 (wet biomass:biofuel) resulted in oil recoveries of greater than 85% based on the lipid class profile. Triglyceride (TG) algal oil was ethylated (EE) and used for oil extraction as well as the parent TG oil (Table 6). All ratios of wet biomass:EE algal oil resulted in oil recoveries of greater than 85% based on the lipid class profile.

TABLE 5

| Wet Biomass:Biofuel Ratio | TG:EE-FFA Ratio | % Algal Oil | Actual % Algal Oil | Oil Recovered (%) |
|---|---|---|---|---|
| Pure Algal Oil | 52.8 | 100 | | |
| 1:2 | 0.0455 | 4.45 | 7.96 | 56 |
| 1:1 | 0.0764 | 7.44 | 14.7 | 51 |
| 1:0.4 | 0.268 | 20.48 | 23.5 | 96 |
| 1:0.2 | 0.42 | 31.42 | 46.4 | 68 |
| Biofuel | 0.00291 | 0 | | |

TABLE 6

| Wet Biomass:Extraction Oil Ratio | Oil Extraction Efficiency (based on mass balance) (%) | Oil Extraction Efficiency (based on DHA:Oleic Acid ratio) (%) |
|---|---|---|
| Biofuel | | |
| 1:2 | 76 | 56 |
| 1:1 | 54 | 51 |
| 1:0.4 | 59 | 96 |
| 1:0.2 | 54 | 68 |
| TG Algal Oil | | |
| 1:2 | 52 | |
| 1:1 | 40 | |
| 1:0.4 | 34 | |
| 1:0.2 | 43 | |
| EE Algal Oil | | |
| 1:2 | 76 | 100 |
| 1:1 | 70 | 100 |
| 1:0.4 | 75 | 100 |
| 1:0.2 | 83 | 100 |

The compositions and methods of the appended claims are not limited in scope by the specific compositions and methods described herein, which are intended as illustrations of a few aspects of the claims and any compositions and methods that are functionally equivalent are within the scope of this disclosure. Various modifications of the compositions and methods in addition to those shown and described herein are intended to fall within the scope of the appended claims. Further, while only certain representative compositions, methods, and aspects of these compositions and methods are specifically described, other compositions and methods and combinations of various features of the compositions and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method of extracting lipids from a population of lipid-producing *Thraustochytrium* microorganisms comprising
    a. contacting the population of lipid-producing microorganisms with one or more enzymes that disrupt the lipid-producing microorganisms, wherein the contacting step is performed in the absence of surfactant and in the presence of the one or more enzymes at a concentration of 0.2% to 0.4% volume/volume; and
    b. extracting lipids from the disrupted lipid-producing microorganisms in the presence of organic solvent, wherein the ratio of disrupted microorganisms to organic solvent is from 1:1 to 1:0.2 volume:volume.

2. The method of claim 1, wherein at least 60% of lipids are extracted from the population of microorganisms.

3. The method of claim 1, wherein at least 90% of lipids are extracted from the population of microorganisms.

4. The method of claim 1, wherein the ratio of disrupted microorganisms to organic solvent is 1:0.2 volume:volume.

5. The method of claim 1, wherein the organic solvent is hexane.

6. The method of claim 1, wherein prior to the contacting step the population of microorganisms is concentrated.

7. The method of claim 6, wherein the population of microorganisms is concentrated by centrifugation.

8. The method of claim 6, wherein the population of microorganisms is concentrated up to 20% solids.

9. The method of claim 6, wherein the population of microorganisms is concentrated from 15% to 20% solids.

10. The method of claim 1, wherein the contacting step is performed at a pH of from 6 to 9.

11. The method of claim 1, wherein the contacting step is performed at a temperature of from 55° C. to 70° C.

12. The method of claim 1, wherein the contacting step is performed at a temperature of from 45° C. to 70° C.

13. The method of claim 1, wherein the contacting step is performed for one to twenty hours.

14. The method of claim 13, wherein the contacting step is performed for four hours.

15. The method of claim 1, wherein the enzyme is a protease.

16. The method of claim 15, wherein the enzyme is an endopeptidase.

17. The method of claim 1, wherein the contacting step is performed for eighteen to twenty hours at 55° C.

18. The method of claim 1, wherein the method lacks a drying step.

19. The method of claim 1, wherein the population of *Thraustochytrium* microorganisms is deposited as ATCC Accession No. PTA-6245.

* * * * *